United States Patent
Yeh

(10) Patent No.: US 11,628,194 B2
(45) Date of Patent: Apr. 18, 2023

(54) METHOD OF EXTRACTING ACTIVE INGREDIENTS IN MUSHROOMS

(71) Applicant: LOHAS BIOTECH DEVELOPMENT CORP., Taipei (TW)

(72) Inventor: Shang-Kaung Yeh, Taipei (TW)

(73) Assignee: LOHAS BIOTECH DEVELOPMENT CORP., Taipei (TW)

( * ) Notice: Subject to any disclaimer, the term of this patent is extended or adjusted under 35 U.S.C. 154(b) by 113 days.

(21) Appl. No.: 17/239,002

(22) Filed: Apr. 23, 2021

(65) Prior Publication Data

US 2022/0339226 A1    Oct. 27, 2022

(51) Int. Cl.
*A61K 36/07* (2006.01)
*A61K 31/015* (2006.01)
*A61K 31/716* (2006.01)

(52) U.S. Cl.
CPC ............ *A61K 36/07* (2013.01); *A61K 31/015* (2013.01); *A61K 31/716* (2013.01); *A61K 2236/15* (2013.01); *A61K 2236/19* (2013.01); *A61K 2236/37* (2013.01); *A61K 2236/53* (2013.01)

(58) Field of Classification Search
None
See application file for complete search history.

(56) References Cited

U.S. PATENT DOCUMENTS

2007/0166320 A1 * 7/2007 Yamazaki .............. A61K 36/07
424/641

FOREIGN PATENT DOCUMENTS

| CN | 104480162 | * | 4/2015 |
| KR | 1687985 | * | 12/2016 |
| KR | 10-2020-0013991 | * | 2/2020 |

OTHER PUBLICATIONS

Leong, Y. et al. Extraction of Polysaccharides from Edible Mushrooms: Emerging Technologies and Recent Advances. Carbohydrate Polymers 251:1-16, 2021. (Year: 2021).*

McCleary, B.V. et al, "Measurement of β-Glucan in Mushrooms and Mycelial Products," J AOAC Int., (2016), 99(2), pp. 364-373 (10 pages).

Wang, Wei et al, "Quantitative Analysis of Triterpenoid in the Mycelia of Ganoderma lucidum" Edible Fungi of China, (2006), vol. 25-1, pp. 30-32, with English abstract (4 pages).

* cited by examiner

*Primary Examiner* — Michael Barker
(74) *Attorney, Agent, or Firm* — Muncy, Geissler, Olds & Lowe, P.C.

(57) ABSTRACT

A method of extracting active ingredients in mushrooms includes following steps: crushing a mushroom to obtain a crude mushroom crush; mixing the crude mushroom crush with deionized water to obtain a crude crush mixture; adding the crude crush mixture into a subcritical fluid extractor and extracting the crude crush mixture to obtain a crude mushroom extract; centrifuging the crude mushroom extract to harvest a first supernatant and a mushroom residue; mixing the mushroom residue with deionized water and a cellulase enzyme to obtain a reaction mixture; adding the reaction mixture into a high-pressure hydrolysis reactor and extracting the reaction mixture to obtain a hydrolysate; centrifuging the hydrolysate to obtain a second supernatant; and combining the first supernatant and the second supernatant, and then concentrating the combined first and second supernatants to obtain a mushroom extraction solution.

13 Claims, 3 Drawing Sheets

METHOD OF EXTRACTING ACTIVE INGREDIENTS IN MUSHROOMS

BACKGROUND

Technology Field

The present disclosure relates to an extraction method for mushrooms and, in particular, to a method of effectively extracting active ingredients from different kinds of mushrooms.

Description of Related Art

Mushrooms contain a variety of special ingredients (such as high-molecular-weight polysaccharides, triterpenes, unsaturated fatty acids, trace elements, flavonoids, etc.), which can strengthen and improve the body's immune system, reduce cancer risk, help control blood glucose and cholesterol levels, resist oxidation, prevent pneumonia, delay dementia symptoms, enhance analgesic effects, improve liver function, and other benefits.

Although mushrooms have many functional components that are beneficial to human bodies, most of them are remained inside cells and protected by the cell wall composed of chitins, which are tough and have complex structure, so that the human bodies are difficult to digest and absorb these effective components. The conventional method of extracting mushrooms is to use hot water extraction, which has the problems of long cooking times, high temperatures and low extraction yields. In order to overcome the shortcomings of conventional hot water extraction, in recent years, various extraction technologies and methods such as ultrasonic- or microwave-assisted extraction, supercritical fluid extraction, and enzyme hydrolysis have been successively derived, but the extraction effects of these methods are also very unsatisfactory. Besides, these conventional extraction methods will use a large amount of organic solvents such as ethanol.

Therefore, it is desired to provide a method of extracting active ingredients in mushrooms that can increase the extraction yield of mushroom, and can avoid the problems of conventional methods such as long cooking time, high temperature, low extraction yield, and the need of substantial amounts of volatile organic solvents.

SUMMARY

An objective of this disclosure is to provide a method of extracting active ingredients in mushrooms. Compared with the conventional art, the method of extracting active ingredients in mushrooms of this disclosure can increase the extraction yield of active ingredients in mushroom, and can avoid the problems of conventional extraction method such as long cooking time, high temperature, low extraction yield, and the need of large amount organic solvents.

To achieve the above, a novel extraction method for mushroom of this disclosure comprises following steps of: a crushing step for crushing a mushroom by a crushing machine to obtain a crude mushroom crush; a mixing step for mixing the crude mushroom crush with deionized water to obtain a crude crush mixture, wherein the crude mushroom crush and the deionized water are fully mixed in a mass-volume ratio of 1:400 to 10:400; a subcritical fluid extraction step for adding the crude crush mixture into a subcritical fluid extractor and extracting the crude crush mixture to obtain a crude mushroom extract, wherein a pressure in the subcritical fluid extractor is between 1000 psi and 5000 psi, an extraction temperature is between 50° C. and 200° C., and an extraction time is between 5 minutes and 40 minutes; a first centrifugal step for centrifuging the crude mushroom extract under 5000~15000 rpm for 5~30 minutes, collecting a supernatant separated from the crude mushroom extract to obtain a first supernatant, and collecting a precipitate separated from the crude mushroom extract to obtain a mushroom residue; a mushroom residue mixing step for fully mixing the mushroom residue with deionized water and a cellulase enzyme to obtain a reaction mixture; a high-pressure hydrolysis step for adding the reaction mixture into a high-pressure hydrolysis reactor and extracting the reaction mixture to obtain a hydrolysate, wherein a pressure in the high-pressure hydrolysis reactor is between 500 psi and 5000 psi, an extraction temperature is between 10° C. and 100° C. and an extraction time is between 10 minutes and 100 minutes; a second centrifugal step for centrifuging the hydrolysate under 5000~15000 rpm for 5~30 minutes, and collecting a supernatant separated from the hydrolysate to obtain a second supernatant; and a concentration step for combining the first supernatant and the second supernatant, and then concentrating a mixture of the first supernatant and the second supernatant under 37° C. to obtain a mushroom extraction solution.

In one embodiment, in the mixing step, the crude mushroom crush and the deionized water are fully mixed in a mass-volume ratio of 3:400 to 9:400.

In one embodiment, in the subcritical fluid extraction step, the pressure in the subcritical fluid extractor is between 1500 psi and 4500 psi, the extraction temperature is between 100° C. and 150° C., and the extraction time is between 10 minutes and 30 minutes.

In one embodiment, in the high-pressure hydrolysis step, the pressure in the high-pressure hydrolysis reactor is between 1000 psi and 3000 psi, the extraction temperature is between 30° C. and 60° C., and the extraction time is between 30 minutes and 90 minutes.

In one embodiment, in the first centrifugal step, the crude mushroom extract is centrifuged under 6000~13000 rpm for 10~20 minutes.

In one embodiment, in the second centrifugal step, the hydrolysate is centrifuged under 6000~13000 rpm for 10~20 minutes.

In one embodiment, in the crushing step, the mushroom is treated by the crushing machine for 10~50 minutes.

In one embodiment, in the crushing step, the mushroom is treated by the crushing machine for 20~30 minutes.

In one embodiment, particle-size distributions of the crude mushroom crush vary between 0.1 mm and 3 mm.

In one embodiment, particle-size distributions of the crude mushroom crush vary between 0.5 mm and 2 mm.

In one embodiment, in the mushroom residue mixing step, the mushroom residue and the deionized water are mixed in a mass-volume ratio of 1:20 to 1:250, and then the cellulase enzyme with a concentration of 0.05~1% is added.

In one embodiment, in the mushroom residue mixing step, the mushroom residue and the deionized water are mixed in the mass-volume ratio of 1:50 to 1:200, and then the cellulase enzyme with a concentration of 0.1~0.6% is added.

In one embodiment, the mushroom extraction solution is rich in β-glucans and triterpenes.

In one embodiment, the mushroom is *Agaricus blazei* Murill, *Phellinus linteus*, or *Tremella fuciformis*.

As mentioned above, the method of extracting active ingredients in mushrooms of this disclosure can increase the extraction yield of active ingredients in mushroom, and can avoid the problems of conventional extraction method such as long cooking time, high temperature, low extraction yield, and the need of large amount organic solvents.

BRIEF DESCRIPTION OF THE DRAWINGS

The disclosure will become more fully understood from the detailed description and accompanying drawings, which are given for illustration only, and thus are not limitative of the present disclosure, and wherein.

DETAILED DESCRIPTION OF THE DISCLOSURE

The present disclosure will be apparent from the following detailed description, which proceeds with reference to the accompanying drawings, wherein the same references relate to the same elements.

A method of extracting active ingredients in mushrooms of this disclosure can increase the extraction yield of active ingredients in mushroom, and can avoid the problems of conventional extraction method such as long cooking time, high temperature, low yield, and the need of large amount organic solvents.

In this disclosure, the mushroom is *Agaricus blazei* Murill, *Phellinus linteus, Tremella fuciformis*, or any mushroom known by those skilled persons in the art.

*Agaricus blazei* Murill (also known as *Agaricus subrufescens*, almond mushroom, or Brazil mushroom) is a kind of edible and medicinal mushroom. It was marketed for its purported medicinal properties under various names, including himematsutake (Japanese), mushroom of the sun (cogumelo do sol), mushroom of God (cogumelo de Deus), and mushroom of life (cogumelo de vida), native to Brazil and Peru with a sweet taste and a fragrance of almonds. Some studies have shown that *Agaricus blazei* Murill contain a variety of special ingredients (such as high-molecular-weight polysaccharides, triterpenoids, unsaturated fatty acids, trace elements, etc.), which can strengthen and improve the body's immune system, reduce cancer risk, help control blood glucose and cholesterol levels, resist oxidation, prevent pneumonia, delay dementia symptoms, enhance analgesic effects, improve liver function, etc.

*Phellinus linteus* (*P. linteus*) is a kind of edible and medicinal mushroom, which grows on the trunk of *Morus* plant. Some studies have shown that *P. linteus* contains a variety of special ingredients (such as high-molecular-weight polysaccharides, triterpenoids, flavonoids, unsaturated fatty acids, trace elements, etc.), which can strengthen and improve the body's immune system, reduce cancer risk, reduce the risk of cardiovascular disease, resist allergies, improve sleep quality, delay dementia symptoms, enhance analgesic effects, improve liver function, etc.

*Tremella fuciformis* is a natural edible and medicinal mushrooms, also known as snow ear, silver ear fungus, and white jelly mushroom, which has a translucent *chrysanthemum* shape or chicken crown shape. Some studies have shown that *Tremella fuciformis* contains a variety of special ingredients (such as high-molecular-weight polysaccharides, triterpenes, trehalose, pentose, mannitol, unsaturated fatty acids, trace elements, etc.). Its nutritional value is high, and it can strengthen and improve the body's immune system, improve respiratory health, activate central nervous system, improve blood circulation, etc.

Figure 1:
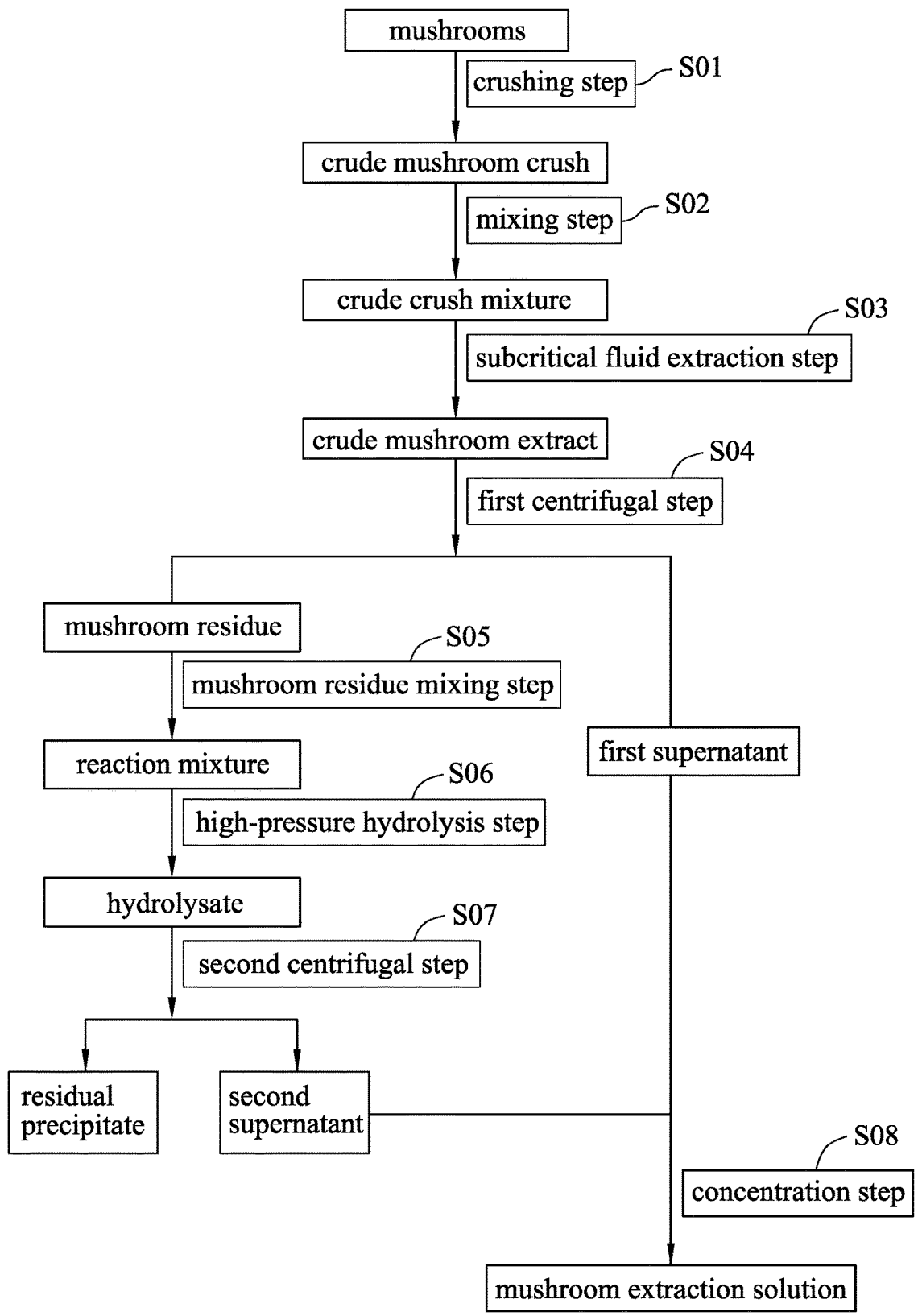
FIG. 1 is a schematic diagram showing a method of extracting active ingredients in mushrooms according to an embodiment of this disclosure.
Figure 2:
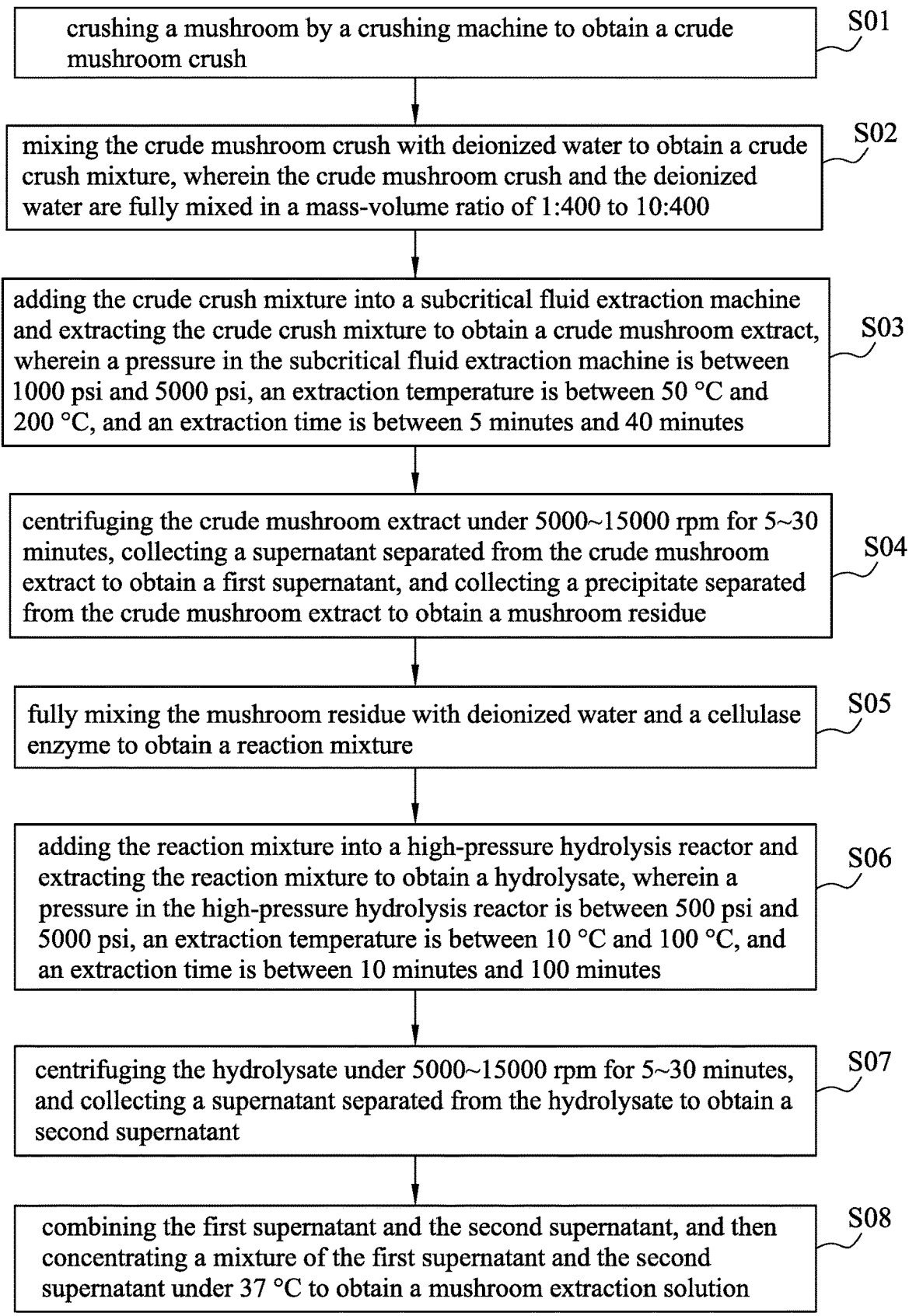
FIG. 2 is a flow chart of the method of extracting active ingredients in mushrooms according to an embodiment of this disclosure.

FIG. 1 is a schematic diagram showing a method of extracting active ingredients in mushrooms according to an embodiment of this disclosure, and FIG. 2 is a flow chart of the method of extracting active ingredients in mushrooms according to an embodiment of this disclosure. Referring to FIGS. 1 and 2, the method of extracting active ingredients in mushrooms of this embodiment comprises the following steps of: a crushing step for crushing a mushroom by a crushing machine to obtain a crude mushroom crush (step S01); a mixing step for mixing the crude mushroom crush with deionized water to obtain a crude crush mixture, wherein the crude mushroom crush and the deionized water are fully mixed in a mass-volume ratio of 1:400 to 10:400 (step S02); a subcritical fluid extraction step for adding the crude crush mixture into a subcritical fluid extractor and extracting the crude crush mixture to obtain a crude mushroom extract, wherein a pressure in the subcritical fluid extractor is between 1000 psi and 5000 psi, an extraction temperature is between 50° C. and 200° C. and an extraction time is between 5 minutes and 40 minutes (step S03); a first centrifugal step for centrifuging the crude mushroom extract under 5000~15000 rpm for 5~30 minutes, collecting a supernatant separated from the crude mushroom extract to obtain a first supernatant, and collecting a precipitate separated from the crude mushroom extract to obtain a mushroom residue (step S04); a mushroom residue mixing step for fully mixing the mushroom residue with deionized water and a cellulase enzyme to obtain a reaction mixture (step S05); a high-pressure hydrolysis step for adding the reaction mixture into a high-pressure hydrolysis reactor and extracting the reaction mixture to obtain a hydrolysate, wherein a pressure in the high-pressure hydrolysis reactor is between 500 psi and 5000 psi, an extraction temperature is between 10° C. and 100° C., and an extraction time is between 10 minutes and 100 minutes (step S06); a second centrifugal step for centrifuging the hydrolysate under 5000~15000 rpm for 5~30 minutes, and collecting a supernatant separated from the hydrolysate to obtain a second supernatant (step S07); and a concentration step for combining the first supernatant and the second supernatant, and then concentrating a mixture of the first supernatant and the second supernatant under 37° C. to obtain a mushroom extraction solution (step S08).

In this embodiment, in the mixing step (step S02), the crude mushroom crush and the deionized water are fully mixed in a mass-volume ratio of 1:400 to 10:400. Preferably, the crude mushroom crush and the deionized water are fully mixed in a mass-volume ratio of 3:400 to 9:400. Preferably, the crude mushroom crush and the deionized water are fully mixed in a mass-volume ratio of 3:400, 4:400, 5:400, 6:400, 7:400, 8:400, or 9:400, or any ratio and range defined between any two of the above-mentioned ratios.

In this embodiment, in the step subcritical fluid extraction step (step S03), the pressure in the subcritical fluid extractor is between 1000 psi and 5000 psi, the extraction temperature is between 50° C. and 200° C., and the extraction time is between 5 minutes and 40 minutes. Preferably, the pressure in the subcritical fluid extractor is between 1500 psi and 4500 psi, the extraction temperature is between 100° C. and 150° C., and the extraction time is between 10 minutes and 30 minutes. Preferably, the pressure in the subcritical fluid extractor can be set to 1500 psi, 2000 psi, 2500 psi, 3000 psi, 3500 psi, 4000 psi, 4500 psi, or any value and range defined between any two of the above-mentioned values. Preferably, the extraction temperature in the subcritical fluid extractor can be set to 100° C., 105° C. 110° C., 115° C., 120° C., 125° C., 130° C., 140° C., 145° C., 150° C., or any value and range defined between any two of the above-mentioned values. Preferably, the extraction time of the subcritical fluid extractor can be set to 10 minutes, 15 minutes, 20 minutes, 25 minutes, 30 minutes, or any value and range defined between any two of the above-mentioned values. The above-mentioned setting conditions of the subcritical fluid extractor are not to limit the scope of this disclosure, and any setting conditions that can sufficiently extract the active ingredients can be used in this disclosure.

In the high-pressure hydrolysis step (step S06) of this embodiment, the pressure in the high-pressure hydrolysis reactor can be set between 500 psi and 5000 psi, the extraction temperature can be set between 10° C. and 100° C. and the extraction time can be set between 10 minutes and 100 minutes. Preferably, the pressure in the high-pressure hydrolysis reactor can be set between 1000 psi and 3000 psi, the extraction temperature can be set between 30° C. and 60° C. and the extraction time can be set between 30 minutes and 90 minutes. Preferably, the pressure in the high-pressure hydrolysis reactor can be set to 1000 psi, 1500 psi, 2000 psi, 2500 psi, 3000 psi, or any value and range defined between any two of the above-mentioned values. Preferably, the extraction temperature in the high-pressure hydrolysis reactor can be set to 30° C. 35° C., 40° C., 45° C., 50° C., 55° C. 60° C., or any value and range defined between any two of the above-mentioned values. Preferably, the extraction time of the high-pressure hydrolysis reactor can be set to 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, or any value and range defined between any two of the above-mentioned values. The above-mentioned setting conditions of the high-pressure hydrolysis reactor are not to limit the scope of this disclosure, and any setting conditions that can sufficiently hydrolysis the reaction mixture can be used in this disclosure.

In the first centrifugal step (step S04) of this embodiment, the crude mushroom extract is centrifuged under 500~15000 rpm for 5~30 minutes. Preferably, the crude mushroom extract is centrifuged under 6000~13000 rpm for 10~20 minutes. Preferably, the crude mushroom extract is centrifuged under 6000 rpm, 6500 rpm, 7000 rpm, 7500 rpm, 8000 rpm, 8500 rpm, 9000 rpm, 9500 rpm, 10000 rpm, 10500 rpm, l1000 rpm, 11500 rpm, 12000 rpm, 12500 rpm, 13000 rpm, or any value and range defined between any two of the above-mentioned rotation speeds, for 10 minutes, 11 minutes, 12 minutes, 13 minutes, 14 minutes, 15 minutes, 16 minutes, 17 minutes, 18 minutes, 19 minutes, 20 minutes, or any value and range defined between any two of the above-mentioned centrifugal times. The above-mentioned setting conditions of the centrifugal step are not to limit the scope of this disclosure, and any setting conditions that can sufficiently separate the supernatant and the precipitate from the crude mushroom extract can be used in this disclosure.

In the second centrifugal step (step S07) of this embodiment, the hydrolysate is centrifuged under 5000~15000 rpm for 5~30 minutes. Preferably, the hydrolysate is centrifuged under 6000~13000 rpm for 10~20 minutes. Preferably, the hydrolysate is centrifuged under 6000 rpm, 6500 rpm, 7000 rpm, 7500 rpm, 8000 rpm, 8500 rpm, 9000 rpm, 9500 rpm, 10000 rpm, 10500 rpm, 11000 rpm, 11500 rpm, 12000 rpm, 12500 rpm, 13000 rpm, or any value and range defined between any two of the above-mentioned rotation speeds, for 10 minutes, 11 minutes, 12 minutes, 13 minutes, 14 minutes, 15 minutes, 16 minutes, 17 minutes, 18 minutes, 19 minutes, 20 minutes, or any value and range defined between any two of the above-mentioned centrifugal times. The above-mentioned setting conditions of the centrifugal step are not to limit the scope of this disclosure, and any setting conditions that can sufficiently separate the supernatant and the precipitate from the hydrolysate can be used in this disclosure.

In the crushing step of this embodiment (step S01), the mushroom can be crushed by a crushing machine for 10~50 minutes. Preferably, the mushroom can be crushed by a crushing machine for 20~30 minutes. Preferably, the mushroom can be crushed by a crushing machine for 20 minutes, 21 minutes, 22 minutes, 23 minutes, 24 minutes, 25 minutes, 26 minutes, 27 minutes, 28 minutes, 29 minutes, 30 minutes, or any value and range defined between any two of the above-mentioned crushing times. Herein, the particle size of the crude mushroom crush is less than or equal to 3 mm, which can facilitate the following subcritical fluid extraction.

In this embodiment, the particle size of the crude mushroom crush can be between 0.1 mm and 3 mm. Preferably, the particle size of the crude mushroom crush can be between 0.5 mm and 2 mm. Preferably, the particle size of the crude mushroom crush can be 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, or any value and range defined between any two of the above-mentioned particle size distributions.

In the mushroom residue mixing step of this embodiment (step S05), the mushroom residue and the deionized water can be fully mixed in a mass-volume ratio of 1:20 to 1:250, and then a cellulase enzyme with a concentration of 0.05~1% is added. Preferably, the mushroom residue and the deionized water can be fully mixed in a mass-volume ratio of 1:50, 1:55, 1:60, 1:65, 1:70, 1:75, 1:80, 1:85, 1:90, 1:95, 1:100, 1:105, 1:110, 1:115, 1:120, 1:125, 1:130, 1:135, 1:140, 1:145, 1:150, 1:155, 1:160, 1:165, 1:170, 1:175, 1:180, 1:185, 1:190, 1:195, 1:200, or any value and range defined between any two of the above-mentioned ratios, and then a cellulase enzyme, with a concentration of 0.1%, 0.2%, 0.3%, 0.4%, 0.5%, 0.6%, or any value and range defined between any two of the above-mentioned concentration percentages, is added.

In this embodiment, the obtained mushroom extraction solution of this embodiment is rich in β-glucans and triterpenes.

Range: Throughout the present disclosure, various embodiments of the present disclosure may be presented in the form of ranges. It should be understood that the description in range format is only for convenience and brevity, and should not be realized as a limitation on the scope of the present disclosure. Therefore, the description of a range should be regarded as specifically disclosing all possible subranges and a single value within the range. For example, the description of a range from 1 to 6 should be considered as including subranges with specific disclosed ranges, such as from 1 to 3, from 1 to 4, from 1 to 5, from 2 to 4, from 2 to 6, from 3 to 6, etc., and a single number or some numbers in this range (e.g. 1, 2, 2.7, 3, 4, 5, 5.3, and 6). The foregoing rules apply regardless of the extent of the range.

The following experimental examples are used to illustrate the method of extracting active ingredients in mushrooms of the present disclosure, which can achieve the effect of significantly increasing the active ingredients in mushroom extracts.

Measurement of active ingredients (β-glucans and triterpenes): Measurement method for β-glucan refers to "Measurement of β-Glucan in Mushrooms and Mycelial Products.", J AOAC Int., 99(2):364-373 (B. V. McCleary et al). Measurement method for triterpenes refers to "Quantitative Analysis of Triterpenoid in the Mycelia of *Ganoderma lucidum*", Edible Fungi of China, Vol. 25-1, p 30-32 (Wei Wang et al).

Measurement of Total Glucan:

(1) Weigh 100 mg mushroom sample into a test tube.

(2) Add 12 M concentrated hydrochloric acid (1.5 mL) to the test tube, lock the cap of the test tube, and stir thoroughly.

(3) Place the test tube in a cold water bath for 2 hours, and stir several times to ensure that the β-glucan is completely dissolved.

(4) Add deionized water (10 mL) to each test tube, cover the test tube, and stir for 20 seconds.

(5) Place the test tube in a boiling water bath (about 100° C.) and react for 2 hours.

(6) Take out the test tube, cool it to room temperature, and carefully loosen the test tube cap.

(7) Quantitatively transfer the content of each test tube to a 100 mL volumetric flask by using 200 mM sodium acetate buffer (pH 5).

(8) Add 2 M potassium hydroxide (10 mL) to the volumetric flask, adjust the volume with 200 mM sodium acetate buffer (pH 5), reverse the volumetric flask to mix the contents therein thoroughly, centrifuge at 13000 rpm for 5 minutes, and collect the supernatant as the test substance.

(9) Take the test substance (0.1 mL) into a glass test tube.

(10) Add 0.1 mL exo-1,3-β-glucanase (100 U/mL) and β-glucosidase (4 U/mL) to each test tube, and react with 200 mM sodium acetate buffer (pH 5) mixture at 40° C. for 60 minutes.

(11) Add glucose oxidase/peroxidase mixture (GOPOD) (3 mL) to each test tube, and react at 40° C. for 20 minutes.

(12) Measure the absorbance at a wavelength of 510 nm with a spectrophotometer.

(13) Calculate the total glucan concentration by the following calculation formula:

Total glucan (%, w/w)=(reaction absorbance−blank absorbance)*(100/*D*-glucose standard absorbance)/weight of sample analyzed*90

Measurement of α-Glucan:

(1) Place the test substance (0.1 mL) in a test tube.

(2) Place a small magnetic rod into each test tube, add 2 M potassium hydroxide (2 mL), and stir in ice-water bath. Add 1.2 M sodium acetate buffer (pH 3.8) (8 mL), amyloglucosidase (1630 U/mL) (0.2 mL) and invertase (500 U/mL) during stirring, and react for 20 minutes.

(3) Place the test tube in a 40° C. water bath and react for 30 minutes.

(4) Centrifuge at 13000 rpm for 3 minutes, and collect the supernatant.

(5) The supernatant (0.1 mL) in a test tube, add 200 mM sodium acetate buffer (pH 5) (0.1 mL) and GOPOD reagent (3 mL), and react at 40° C. for 20 minutes.

(6) Measure the absorbance at a wavelength of 510 nm with a spectrophotometer.

(7) Calculate the concentration of α-glucan by the following calculation formula:

(when the final volume is 100 mL): α-glucan (%, w/w)=(reaction absorbance−blank absorbance)* (100/*D*-glucose standard absorbance)/weight of sample analyzed*90

(when the final volume is 10.3 mL): α-glucan (%, w/w)=(reaction absorbance-blank absorbance)* (100/*D*-glucose standard absorbance)/weight of sample analyzed*9.27

Calculation of β-glucan content: Measure the concentration of total glucan and α-glucan by the above methods, and then subtract the α-glucan from the total glucan to obtain the calculated value of β-glucan. The calculation formula is as follow:

β-glucan=(total glucan)−(α-glucan)

Measurement of Triterpene Content:

(1) 1 mL of standard oleanolic acid of different concentrations or the mushroom samples in a test tube, place in a water bath at 100° C., evaporate to dry, and stay at room temperature.

(2) Add 5% vanillin-glacial acetic acid (0.3 mL) and perchloric acid (1 mL), and mix thoroughly.

(3) Heat in a 70° C. water bath for 25 minutes, move into an iced-water bath to cool for 3 minutes, and take out to room temperature.

(4) Add glacial acetic acid (10 mL), mix thoroughly, and react at room temperature for 15 minutes.

Figure 3:
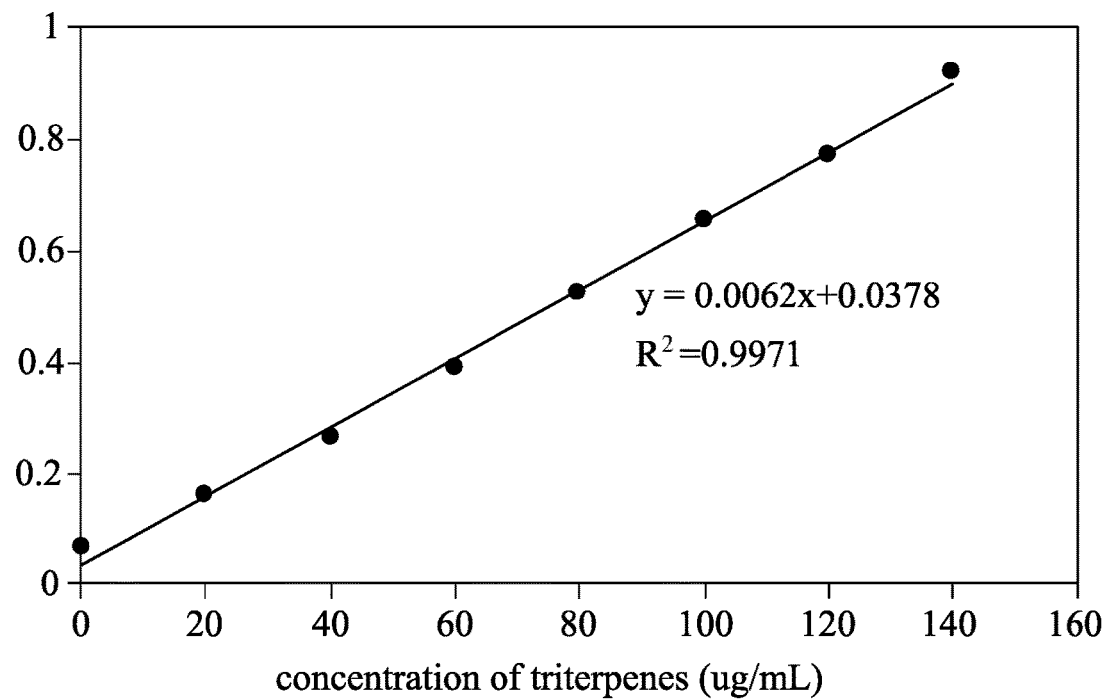
FIG. 3 is a schematic diagram showing the standard curve of triterpenes based on absorption at 550 nm.

(5) Measure the absorbance of different concentrations of oleanolic acid standards or the mushroom samples with a spectrophotometer at 550 nm. Draw the triterpene standard curve based on different concentrations of oleanolic acid (see FIG. 3), substitute the absorbance of the mushroom samples into the linear regression equation of the triterpene standard curve to calculate the amount of triterpenes in mushroom extracts.

The following are different experimental examples of extracting active ingredients from *Agaricus blazei* Murill using the method of extracting active ingredients from mushrooms of the present disclosure:

Experimental Example 1

The fresh fruit bodies of *Agaricus blazei* Murill are crushed by a crushing machine to obtain a crude mushroom crush of *Agaricus blazei* Murill. Then, the crude mushroom crush is fully mixed with deionized water in a mass-volume ratio of 3:400 to obtain a crude crush mixture. Next, the crude crush mixture is added into a subcritical fluid extractor and extracted to obtain a crude mushroom extract, wherein the pressure in the subcritical fluid extractor is 1500 psi, the extraction temperature is 100° C., and the extraction time is 10 minutes. The crude mushroom extract is centrifuged at 6000 rpm for 20 minutes, followed by collecting a supernatant separated from the crude mushroom extract to obtain a first supernatant, and collecting a precipitate separated from the crude mushroom extract to obtain a mushroom residue. Then, the mushroom residue is fully mixed with deionized water in a mass-volume ratio of 1:50, and a cellulase enzyme with a concentration of 1% is added and fully mixed to obtain a reaction mixture. The reaction mixture is added into a high-pressure hydrolysis reactor and extracted to obtain a hydrolysate, wherein the pressure in the high-pressure hydrolysis reactor is 1000 psi, the extraction temperature is 30° C., and the extraction time is 30 minutes. Afterwards, the hydrolysate is centrifuged at 6000 rpm for 20 minutes, followed by collecting a supernatant separated from the hydrolysate to obtain a second supernatant, and removing the residual precipitate. Finally, the first supernatant and the second supernatant are combined, and then the combined mixture of the first supernatant and the second supernatant is (vacuum) concentrated at 37° C. to twice the weight of raw material (w/w), so as to obtain a mushroom (*Agaricus blazei* Murill) extraction solution.

Experimental Example 2

The fresh fruit bodies of *Agaricus blazei* Murill are crushed by a crushing machine to obtain a crude mushroom crush of *Agaricus blazei* Murill. Then, the crude mushroom crush is fully mixed with deionized water in a mass-volume ratio of 9:400 to obtain a crude crush mixture. Next, the crude crush mixture is added into a subcritical fluid extractor and extracted to obtain a crude mushroom extract, wherein the pressure in the subcritical fluid extractor is 1500 psi, the extraction temperature is 150° C., and the extraction time is 30 minutes. The crude mushroom extract is centrifuged at 6000 rpm for 20 minutes, followed by collecting a supernatant separated from the crude mushroom extract to obtain a first supernatant, and collecting a precipitate separated from the crude mushroom extract to obtain a mushroom residue. Then, the mushroom residue is fully mixed with deionized water in a mass-volume ratio of 1:50, and a cellulase enzyme with a concentration of 0.6% is added and fully mixed to obtain a reaction mixture. The reaction mixture is added into a high-pressure hydrolysis reactor and extracted to obtain a hydrolysate, wherein the pressure in the high-pressure hydrolysis reactor is 1000 psi, the extraction temperature is 60° C., and the extraction time is 90 minutes. Afterwards, the hydrolysate is centrifuged at 6000 rpm for 20 minutes, followed by collecting a supernatant separated from the hydrolysate to obtain a second supernatant, and removing the residual precipitate. Finally, the first supernatant and the second supernatant are combined, and then the combined mixture of the first supernatant and the second supernatant is (vacuum) concentrated at 37° C. to twice the weight of raw material (w/w), so as to obtain a mushroom (*Agaricus blazei* Murill) extraction solution.

Experimental Example 3

The fresh fruit bodies of *Agaricus blazei* Murill are crushed by a crushing machine to obtain a crude mushroom crush of *Agaricus blazei* Murill. Then, the crude mushroom crush is fully mixed with deionized water in a mass-volume ratio of 6:400 to obtain a crude crush mixture. Next, the crude crush mixture is added into a subcritical fluid extractor and extracted to obtain a crude mushroom extract, wherein the pressure in the subcritical fluid extractor is 3000 psi, the extraction temperature is 150° C., and the extraction time is 10 minutes. The crude mushroom extract is centrifuged at 6000 rpm for 20 minutes, followed by collecting a supernatant separated from the crude mushroom extract to obtain a first supernatant, and collecting a precipitate separated from the crude mushroom extract to obtain a mushroom residue. Then, the mushroom residue is fully mixed with deionized water in a mass-volume ratio of 1:50, and a cellulase enzyme with a concentration of 0.3% is added and fully mixed to obtain a reaction mixture. The reaction mixture is added into a high-pressure hydrolysis reactor and extracted to obtain a hydrolysate, wherein the pressure in the high-pressure hydrolysis reactor is 2000 psi, the extraction temperature is 60° C., and the extraction time is 30 minutes. Afterwards, the hydrolysate is centrifuged at 6000 rpm for 20 minutes, followed by collecting a supernatant separated from the hydrolysate to obtain a second supernatant, and removing the residual precipitate. Finally, the first supernatant and the second supernatant are combined, and then the combined mixture of the first supernatant and the second supernatant is (vacuum) concentrated at 37° C. to twice the weight of raw material (w/w), so as to obtain a mushroom (*Agaricus blazei* Murill) extraction solution.

Experimental Example 4

The fresh fruit bodies of *Agaricus blazei* Murill are crushed by a crushing machine to obtain a crude mushroom crush of *Agaricus blazei* Murill. Then, the crude mushroom crush is fully mixed with deionized water in a mass-volume ratio of 9:400 to obtain a crude crush mixture. Next, the crude crush mixture is added into a subcritical fluid extractor and extracted to obtain a crude mushroom extract, wherein the pressure in the subcritical fluid extractor is 3000 psi, the extraction temperature is 100° C., and the extraction time is 20 minutes. The crude mushroom extract is centrifuged at 6000 rpm for 20 minutes, followed by collecting a supernatant separated from the crude mushroom extract to obtain a first supernatant, and collecting a precipitate separated from the crude mushroom extract to obtain a mushroom residue. Then, the mushroom residue is fully mixed with deionized water in a mass-volume ratio of 1:50, and a cellulase enzyme with a concentration of 0.6% is added and fully mixed to obtain a reaction mixture. The reaction mixture is added into a high-pressure hydrolysis reactor and extracted to obtain a hydrolysate, wherein the pressure in the high-pressure hydrolysis reactor is 2000 psi, the extraction temperature is 30° C., and the extraction time is 60 minutes. Afterwards, the hydrolysate is centrifuged at 6000 rpm for 20 minutes, followed by collecting a supernatant separated from the hydrolysate to obtain a second supernatant, and removing the residual precipitate. Finally, the first supernatant and the second supernatant are combined, and then the combined mixture of the first supernatant and the second supernatant is (vacuum) concentrated at 37° C. to twice the weight of raw material (w/w), so as to obtain a mushroom (*Agaricus blazei* Murill) extraction solution.

Experimental Example 5

The fresh fruit bodies of *Agaricus blazei* Murill are crushed by a crushing machine to obtain a crude mushroom crush of *Agaricus blazei* Murill. Then, the crude mushroom crush is fully mixed with deionized water in a mass-volume ratio of 3:400 to obtain a crude crush mixture. Next, the crude crush mixture is added into a subcritical fluid extractor and extracted to obtain a crude mushroom extract, wherein the pressure in the subcritical fluid extractor is 4500 psi, the extraction temperature is 150° C., and the extraction time is 20 minutes. The crude mushroom extract is centrifuged at 6000 rpm for 20 minutes, followed by collecting a supernatant separated from the crude mushroom extract to obtain a first supernatant, and collecting a precipitate separated from the crude mushroom extract to obtain a mushroom residue. Then, the mushroom residue is fully mixed with deionized water in a mass-volume ratio of 1:50, and a cellulase enzyme with a concentration of 0.1% is added and fully mixed to obtain a reaction mixture. The reaction mixture is added into a high-pressure hydrolysis reactor and extracted to obtain a hydrolysate, wherein the pressure in the high-pressure hydrolysis reactor is 3000 psi, the extraction temperature is 60° C., and the extraction time is 60 minutes. Afterwards, the hydrolysate is centrifuged at 6000 rpm for 20 minutes, followed by collecting a supernatant separated from the hydrolysate to obtain a second supernatant, and removing the residual precipitate. Finally, the first supernatant and the second supernatant are combined, and then the combined mixture of the first supernatant and the second supernatant is (vacuum) concentrated at 37° C. to twice the weight of raw material (w/w), so as to obtain a mushroom (*Agaricus blazei* Murill) extraction solution.

Experimental Example 6

The fresh fruit bodies of *Agaricus blazei* Murill are crushed by a crushing machine to obtain a crude mushroom crush of *Agaricus blazei* Murill. Then, the crude mushroom crush is fully mixed with deionized water in a mass-volume ratio of 6:400 to obtain a crude crush mixture. Next, the crude crush mixture is added into a subcritical fluid extractor and extracted to obtain a crude mushroom extract, wherein the pressure in the subcritical fluid extractor is 4500 psi, the extraction temperature is 100° C., and the extraction time is 30 minutes. The crude mushroom extract is centrifuged at 6000 rpm for 20 minutes, followed by collecting a supernatant separated from the crude mushroom extract to obtain a first supernatant, and collecting a precipitate separated from the crude mushroom extract to obtain a mushroom residue. Then, the mushroom residue is fully mixed with deionized water in a mass-volume ratio of 1:50, and a cellulase enzyme with a concentration of 0.3% is added and fully mixed to obtain a reaction mixture. The reaction mixture is added into a high-pressure hydrolysis reactor and extracted to obtain a hydrolysate, wherein the pressure in the high-pressure hydrolysis reactor is 3000 psi, the extraction temperature is 30° C., and the extraction time is 90 minutes. Afterwards, the hydrolysate is centrifuged at 6000 rpm for 20 minutes, followed by collecting a supernatant separated from the hydrolysate to obtain a second supernatant, and removing the residual precipitate. Finally, the first supernatant and the second supernatant are combined, and then the combined mixture of the first supernatant and the second supernatant is (vacuum) concentrated at 37° C. to twice the weight of raw material (w/w), so as to obtain a mushroom (*Agaricus blazei* Murill) extraction solution.

Experimental Example 7

The fresh fruit bodies of *Agaricus blazei* Murill are crushed by a crushing machine to obtain a crude mushroom crush of *Agaricus blazei* Murill. Then, the crude mushroom crush is fully mixed with deionized water in a mass-volume ratio of 9:400 to obtain a crude crush mixture. Next, the crude crush mixture is added into a subcritical fluid extractor and extracted to obtain a crude mushroom extract, wherein the pressure in the subcritical fluid extractor is 4500 psi, the extraction temperature is 125° C., and the extraction time is 10 minutes. The crude mushroom extract is centrifuged at 6000 rpm for 20 minutes, followed by collecting a supernatant separated from the crude mushroom extract to obtain a first supernatant, and collecting a precipitate separated from the crude mushroom extract to obtain a mushroom residue. Then, the mushroom residue is fully mixed with deionized water in a mass-volume ratio of 1:50, and a cellulase enzyme with a concentration of 0.6% is added and fully mixed to obtain a reaction mixture. The reaction mixture is added into a high-pressure hydrolysis reactor and extracted to obtain a hydrolysate, wherein the pressure in the high-pressure hydrolysis reactor is 3000 psi, the extraction temperature is 45° C., and the extraction time is 30 minutes. Afterwards, the hydrolysate is centrifuged at 6000 rpm for 20 minutes, followed by collecting a supernatant separated from the hydrolysate to obtain a second supernatant, and removing the residual precipitate. Finally, the first supernatant and the second supernatant are combined, and then the combined mixture of the first supernatant and the second supernatant is (vacuum) concentrated at 37° C. to twice the weight of raw material (w/w), so as to obtain a mushroom (*Agaricus blazei* Murill) extraction solution.

Experimental Example 8

The fresh fruit bodies of *Agaricus blazei* Murill are crushed by a crushing machine to obtain a crude mushroom crush of *Agaricus blazei* Murill. Then, the crude mushroom crush is fully mixed with deionized water in a mass-volume ratio of 3:400 to obtain a crude crush mixture. Next, the crude crush mixture is added into a subcritical fluid extractor and extracted to obtain a crude mushroom extract, wherein the pressure in the subcritical fluid extractor is 3000 psi, the extraction temperature is 100° C., and the extraction time is 30 minutes. The crude mushroom extract is centrifuged at 6000 rpm for 20 minutes, followed by collecting a supernatant separated from the crude mushroom extract to obtain a first supernatant, and collecting a precipitate separated from the crude mushroom extract to obtain a mushroom residue. Then, the mushroom residue is fully mixed with deionized water in a mass-volume ratio of 1:50, and a cellulase enzyme with a concentration of 0.3% is added and fully mixed to obtain a reaction mixture. The reaction mixture is added into a high-pressure hydrolysis reactor and extracted to obtain a hydrolysate, wherein the pressure in the high-pressure hydrolysis reactor is 3000 psi, the extraction temperature is 30° C., and the extraction time is 60 minutes. Afterwards, the hydrolysate is centrifuged at 6000 rpm for 20 minutes, followed by collecting a supernatant separated from the hydrolysate to obtain a second supernatant, and removing the residual precipitate. Finally, the first supernatant and the second supernatant are combined, and then the combined mixture of the first supernatant and the second supernatant is (vacuum) concentrated at 37° C. to twice the weight of raw material (w/w), so as to obtain a mushroom (*Agaricus blazei* Murill) extraction solution.

The *Agaricus blazei* Murill extraction solution obtained in above experimental examples 1 to 8 were measured to determine the contents of β-glucan and triterpenes therein according to the above method. The detection results are shown in the following Table 1.

TABLE 1

| *Agaricus blazei* Murill extraction solution | content of β-glucan (%) | content of triterpene (%) |
| --- | --- | --- |
| experimental example 1 | 3.92 ± 0.21 | 0.43 ± 0.04 |
| experimental example 2 | 3.83 ± 0.05 | 0.79 ± 0.09 |
| experimental example 3 | 3.05 ± 0.18 | 0.65 ± 0.03 |
| experimental example 4 | 3.01 ± 0.06 | 0.51 ± 0.04 |
| experimental example 5 | 2.42 ± 0.27 | 0.83 ± 0.16 |
| experimental example 6 | 3.25 ± 0.16 | 0.58 ± 0.07 |
| experimental example 7 | 2.05 ± 0.05 | 0.57 ± 0.11 |
| experimental example 8 | 4.16 ± 0.22 | 0.53 ± 0.08 |

As shown in the above Table 1, the *Agaricus blazei* Murill extraction solution obtained by the method of extracting active ingredients in mushrooms of the present disclosure is rich in β-glucans and triterpenes. The extractable β-glucan content in the total amount of *Agaricus blazei* Murill extraction solution can reach 2% or more, and the triterpene content s in extraction solution can reach 0.39% or more.

To be noted, although the above experimental examples take the extraction of *Agaricus blazei* Murill as an example for illustration, they are not a limitation of the present disclosure. The method of extracting active ingredients in mushrooms of the present disclosure can also be used to extract *Phellinus linteus, Tremella fuciformis*, or any mushroom known by those skilled persons in the art.

In summary, the method of extracting active ingredients in mushrooms of this disclosure can increase the extraction yield, and can avoid the problems of conventional method such as long cooking time, high temperature, low extraction yield, and the need of large amount organic solvents.

Although the disclosure has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the disclosure.

What is claimed is:

1. An extraction method for mushroom, comprising steps of:
   a crushing step for crushing a mushroom by a crushing machine to obtain a crude mushroom crush;
   a mixing step for mixing the crude mushroom crush with deionized water to obtain a crude crush mixture, wherein the crude mushroom crush and the deionized water are fully mixed in a mass-volume ratio of 1:400 to 10:400;
   a subcritical fluid extraction step for adding the crude crush mixture into a subcritical fluid extractor and extracting the crude crush mixture to obtain a crude mushroom extract, wherein a pressure in the subcritical fluid extractor is between 1000 psi and 5000 psi, an extraction temperature is between 50° C. and 200° C., and an extraction time is between 5 minutes and 40 minutes;
   a first centrifugal step for centrifuging the crude mushroom extract under 5000~15000 rpm for 5~30 minutes, collecting a supernatant separated from the crude mushroom extract to obtain a first supernatant, and collecting a precipitate separated from the crude mushroom extract to obtain a mushroom residue;
   a mushroom residue mixing step for fully mixing the mushroom residue with deionized water and a cellulase enzyme to obtain a reaction mixture;
   a high-pressure hydrolysis step for adding the reaction mixture into a high-pressure hydrolysis reactor and extracting the reaction mixture to obtain a hydrolysate, wherein a pressure in the high-pressure hydrolysis reactor is between 500 psi and 5000 psi, an extraction temperature is between 10° C. and 100° C., and an extraction time is between 10 minutes and 100 minutes;
   a second centrifugal step for centrifuging the hydrolysate under 5000~15000 rpm for 5~30 minutes, and collecting a supernatant separated from the hydrolysate to obtain a second supernatant; and
   a concentration step for combining the first supernatant and the second supernatant, and then concentrating a mixture of the first supernatant and the second supernatant under 37° C. to obtain a mushroom extraction solution;
   wherein the mushroom is *Agaricus blazei* Murill, *Phellinus linteus*, or *Tremella fuciformis*.

2. The extraction method of claim 1, wherein in the mixing step, the crude mushroom crush and the deionized water are fully mixed in a mass-volume ratio of 3:400 to 9:400.

3. The extraction method of claim 1, wherein in the subcritical fluid extraction step, the pressure in the subcritical fluid extractor is between 1500 psi and 4500 psi, the extraction temperature is between 100° C. and 150° C., and the extraction time is between 10 minutes and 30 minutes.

4. The extraction method of claim 1, wherein in the high-pressure hydrolysis step, the pressure in the high-pressure hydrolysis reactor is between 1000 psi and 3000 psi, the extraction temperature is between 30° C. and 60° C., and the extraction time is between 30 minutes and 90 minutes.

5. The extraction method of claim 1, wherein in the first centrifugal step, the crude mushroom extract is centrifuged under 6000~13000 rpm for 10~20 minutes.

6. The extraction method of claim 1, wherein in the second centrifugal step, the hydrolysate is centrifuged under 6000~13000 rpm for 10~20 minutes.

7. The extraction method of claim 1, wherein in the crushing step, the mushroom is treated by the crushing machine for 10~50 minutes.

8. The extraction method of claim 7, wherein in the crushing step, the mushroom is treated by the crushing machine for 20~30 minutes.

9. The extraction method of claim 1, wherein particle-size distributions of the crude mushroom crush vary between 0.1 mm and 3 mm.

10. The extraction method of claim 9, wherein particle-size distributions of the crude mushroom crush vary between 0.5 mm and 2 mm.

11. The extraction method of claim 1, wherein in the mushroom residue mixing step, the mushroom residue and the deionized water are mixed in a mass-volume ratio of 1:20 to 1:250, and then the cellulase enzyme with a concentration of 0.05~1% is added.

12. The extraction method of claim 11, wherein in the mushroom residue mixing step, the mushroom residue and the deionized water are mixed in the mass-volume ratio of 1:50 to 1:200, and then the cellulase enzyme with a concentration of 0.1~0.6% is added.

13. The extraction method of claim 1, wherein the mushroom extraction solution is rich in β-glucans and triterpenes.

* * * * *